United States Patent [19]
Allor

[11] 4,261,369
[45] Apr. 14, 1981

[54] HIS BUNDLE CARDIOGRAPHY

[76] Inventor: Douglas R. Allor, 1143 Beaconsfield, Apt. 5, Grosse Pointe Park, Mich. 48230

[21] Appl. No.: 12,071

[22] Filed: Feb. 14, 1979

[51] Int. Cl.³ .............................................. A61B 5/04
[52] U.S. Cl. .................................................. 128/696
[58] Field of Search ............... 128/695, 696, 700, 701, 128/708, 709, 710, 712, 715, 901, 902, 903

[56] References Cited

U.S. PATENT DOCUMENTS 4,157,711   6/1979   Yotam et al. ......................... 128/712

OTHER PUBLICATIONS

Berbari et al., "Circulation", vol. 48, Nov. 1973, pp. 1005-1012.
Flowers et al., "American Journal of Cardiology", vol. 33, Mar. 1974, pp. 384-389.
Wajszczuk et al., "Circulation", vol. 58 #1, Jul. 1978, pp. 95-102.
Mauser, "Electronik", vol. 26, No. 2, Feb. 1977, pp. 51-54.
Duffin, Jr. et al., "Proceedings of the 23rd Annual Conference on Engineering in Medicine & Biology", Wash., D.C., 16-19, Nov. 1970, p. 193.
Siegel et al., "IEEE Transactions on Biomedical Engineering", vol. 22, No. 4, Jul. 1975, pp. 269-274.

Primary Examiner—William E. Kamm
Attorney, Agent, or Firm—Barnes, Kisselle, Raisch & Choate

[57] ABSTRACT

A non-invasive technique for monitoring the atrioventricular His bundle electrocardiogram and recording the same on a strip chart recorder in parallel real time with a conventional surface ECG signal. The preferred embodiment of the His bundle circuitry includes separately adjustable highpass and lowpass filters in the frequency range of 30 to 600 Hz, and a variable gain amplifier for in situ empirical adjustment to patient and environmental conditions.

16 Claims, 4 Drawing Figures

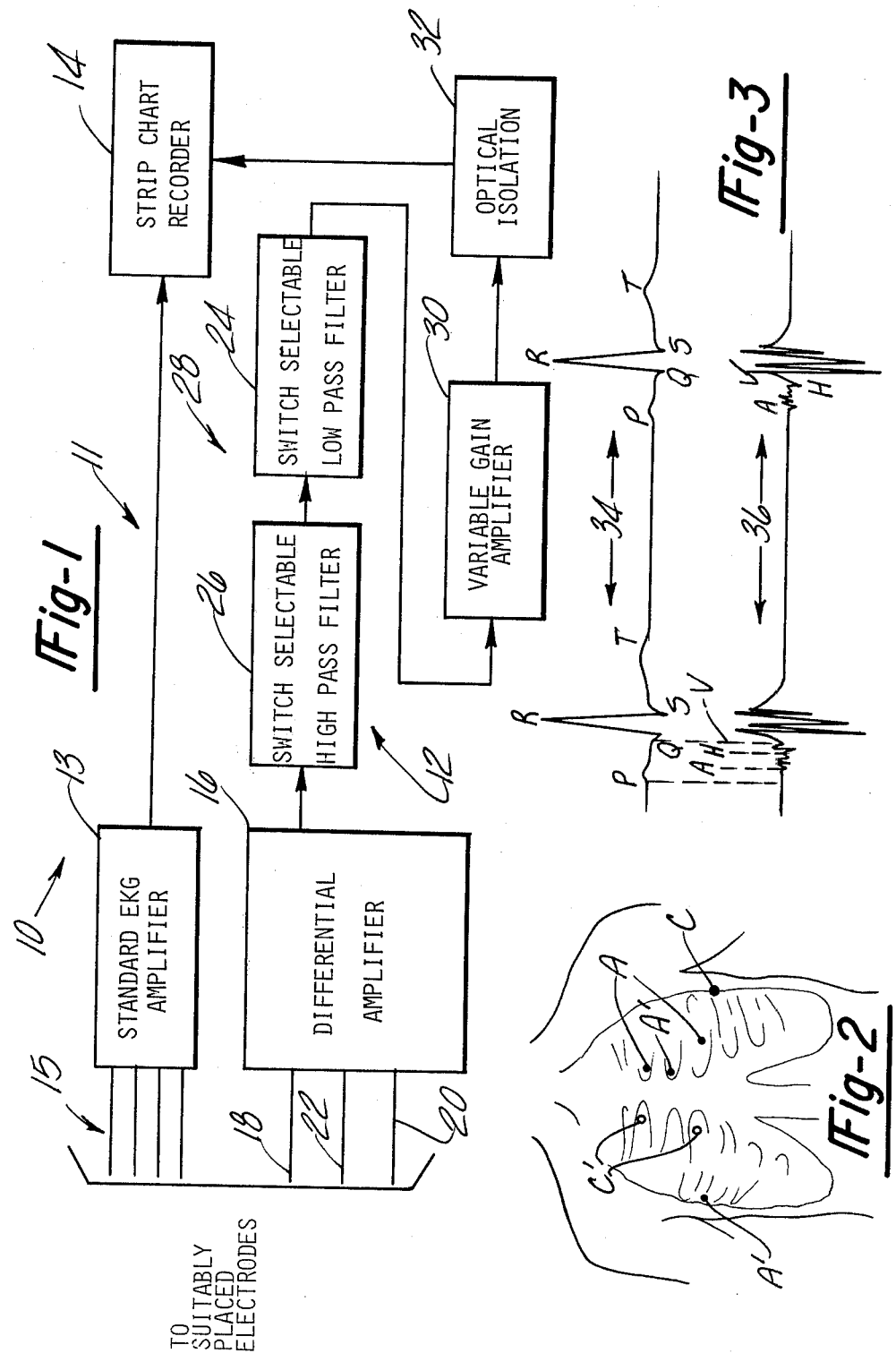

HIS BUNDLE CARDIOGRAPHY

The present invention is directed to electrocardiography, and more particularly to clinical analysis of the atrioventricular and intraventricular cardiac conduction system. Yet more specifically, the invention relates to non-invasive monitoring and recording of the His-Purkinje electrocardiogram.

Accepted techniques for recording the signals in the His bundle and Purkinje network for clinical diagnostic purposes involve percutaneous insertion of an electrode catheter into the femoral vein and advancement of the catheter into the right ventricle of the heart. This procedure, although clinically accepted and generally painless, can have a traumatic effect upon the patient. An attempt at non-invasive His bundle cardiography is described in Wajszczuk et al, "Non-invasive Recording of His-Purkinje Activity in Man by QRS-Triggered Signal Averaging", *Circulation*, July 1978. This technique involves high gain amplification ($10_5$) of His bundle signals from surface ECG chest-type electrodes as triggered by the next-subsequent QRS signal, bandpass filtering (30 to 300 Hz), analog-to-digital conversion and then averaging of the His signals over a number (128 or 256) of consecutive samples to obtain an acceptable signal-to-noise ratio. However, failure of this technique to provide monitoring and recording on a beat-for-beat basis in real time renders the same inadequate for clinical diagnosis of a significant number of intermittent pathological events.

Accordingly, a general object of the present invention is to provide a method, apparatus and/or system for non-invasively monitoring and continuously recording the His bundle signal on a beat-for-beat basis.

Another object of the invention is to provide a method, apparatus and/or system for simultaneously monitoring and continuously recording the His bundle and surface ECG signals independently of each other for more reliable clinical diagnosis.

A further object of the invention is to provide a His bundle signal amplifier which includes provision for in situ empirical selection of amplifier filtering and/or gain characteristics to accommodate varying lead placement and patient conditions. Yet another object of the invention is to provide a His bundle signal amplifier of the type described which may be utilized in combination with standard surface ECG-type "stress test" chest electrodes. (Persons skilled in the electrocardiographic arts will recognize that "stress test" is a generic term applied in the art to a particular type of disposable electrode marketed by American Hospital Supply Corporation and numerous others.)

The invention, together with additional objects, features and advantages thereof, will be best understood from the following description, the appended claims and the accompanying drawings in which:

FIG. 1 is a functional block diagram of a presently preferred embodiment of the invention for parallel recording of the His bundle and surface ECG signals in real time;

FIG. 2 is a chest diagram illustrating preferred locations for electrode placement in accordance with one aspect of the invention;

FIG. 3 is a diagram illustrating waveforms recorded in accordance with the invention.

Figure 4:
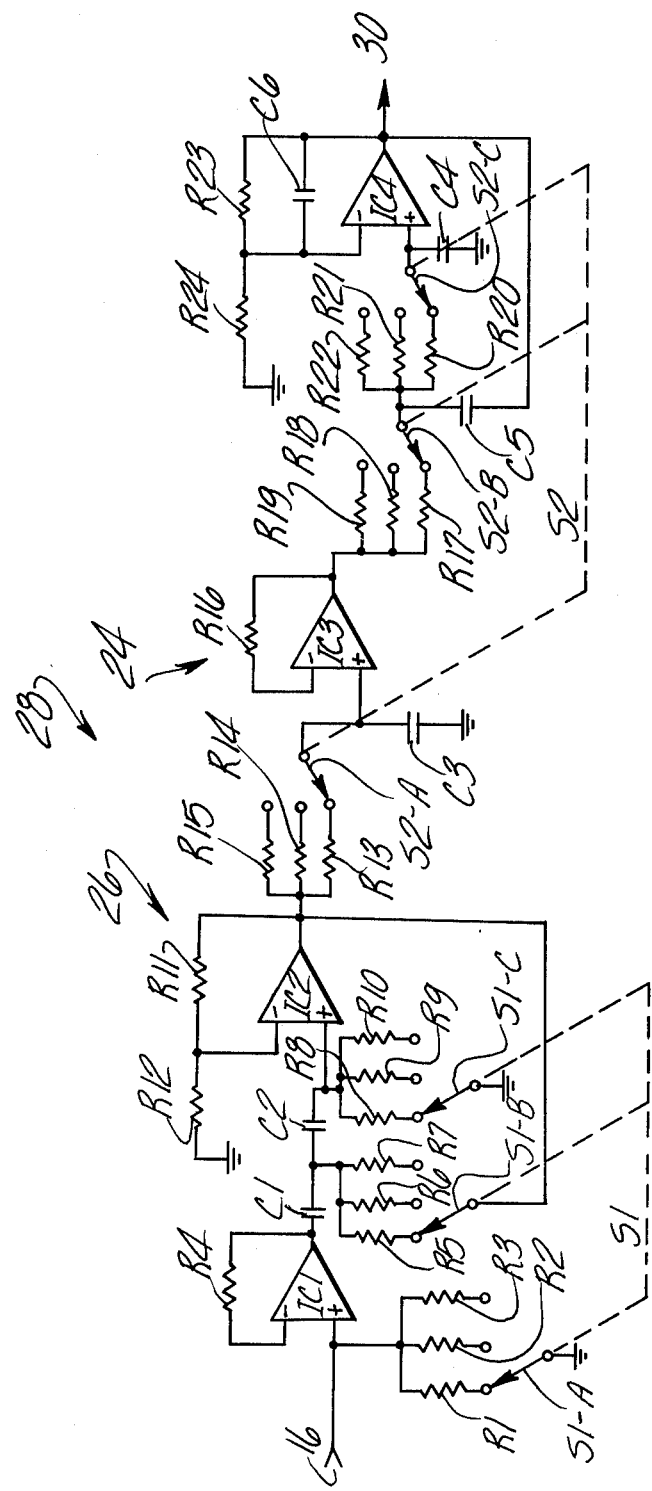
FIG. 4 is an electrical schematic drawing of presently preferred embodiments of the low and highpass filters illustrated in FIG. 1.

By way of background, the atrioventricular conduction system of the human heart is divided for purposes of clinical analysis into a number of specialized portions: (1) the A-V node, (2) the His bundle, (3) the left and right bundle branches, and (4) the Purkinje fiber networks. The present invention deal with monitoring and recording for purposes of clinical analysis the progression of electrical signals from the A-V node to the Purkinje fiber network. This signal progression is referenced collectively herein as the His bundle electrocardiogram or the atrioventricular electrocardiogram, which terms are considered synonamous for purposes of the instant application. Techniques for clinical diagnosis of the His bundle electrocardiogram, either alone or in conjunction with the conventional surface ECG, are the subject of a number of texts and treatises, and will not be discussed in detail herein. To the contrary, the relationship of the His bumdle and surface electrocardiogram will only be outlined herein in connection with FIG. 2 for the purpose of outlining operation of the invention.

FIG. 1 illustrates a preferred system 10 in accordance with the invention for parallel continuous recording of surface and His bundle electrocardiograms in real time. System 10 generally includes parallel channels 12,11 respectively for sensing the analog His bundle and surface ECG signals, providing suitable amplification, and directing such signals to corresponding channels of a multiple channel strip chart recorder 14. Sensing channels 11,12 are electrically independent of each other, as distinguished from the above-referenced Wajszczuk proposal wherein a surface ECG signal triggers or enables His bundle recording. Moreover, strip chart recorder 14 receives the respective analog signals from channels 11, 12 and records the same in real time on a single recording sheet with a common time base to facilitate clinical analysis of intermittent pathological events.

In channel 11, an amplifier 13 is connected by the leads 15 to limb or chest electrodes suitably placed by a technician onto a patient for sensing and amplifying the surface analog ECG signal, and for directing such signal to one input channel of multiple recorder 14. Amplifier 10 may be of any conventional configuration. In channel 12, differential amplifier 16, having an input impedance on the preferred order of 130 to 140 megohms and high common mode rejection, has the differentially-connected input signal leads 18,20 and a common lead 22 connected to stress-type chest electrodes suitably placed on a patient's chest. (Preferred electrode placement will be discussed hereinafter in connection with FIG. 2.) The output of differential amplifier 16 is connected to a bandpass filtering arrangement 28 comprising separate switch-selectable lowpass and highpass series-connected filter circuits 24,26. The output of filter 28 is connected to variable gain amplifier 30 having a maximum gain on the order of $10^6$. The output of amplifier 30 is connected through an optical isolation module 32 to a second input recording channel of recorder 14.

Typical waveforms recorded by recorder 14 are illustrated in FIG. 3. A surface ECG signal waveform for a normal or "healthy" patient is illustrated at 34 in FIG. 3 as comprising P, Q, R, S and T signal components of successively alternating polarity. Amplitude of the surface ECG signal ranges typically from between 50 to 100 microvolts for the P and T components to on the order of one millivolt for the R signal component. A typical surface ECG signal would possess a frequency range of 0.01 to 100 Hz.

A typical His bundle signal recorded in accordance with the invention and illustrated at 36, on the other hand, may possess a maximum amplitude of less than five microvolts and a frequency range of 30 to 500 Hz. The first deflection in His bundle signal represents atrial activation (A wave) in the area of the low atrial septum at the A-V junction on the heart. This atrial activation is coincident with the middle portion of the P or atrial depolarization signal component as seen on the surface ECG leads. The second deflection of His bundle signal 36, representing His bundle activation (H), is usually a bi- or triphasic rapid deflection occurring during the isoelectric portion of the P-R segment as seen in the surface ECG leads. The third deflection of the His bundle electrogram 36 represents activation of the ventricles (V). This potential coincides with the QRS or ventricular depolarization signal complex.

Thus, the His bundle electrogram, in conjunction with the simultaneously recorded surface ECG, allows a division of the P-R interval in recording 34 into three components for purposes of clinical analysis: (1) The P-A interval, which is measured from the earliest onset of the P wave in surface electrocardiogram 34 to the beginning of the A wave is recording 36. This interval corresponds to a representative portion of the intra-atrial conduction between the area of the sinus node and the area of the A-V junction, and may typically be on the order of thirty-five milliseconds. (2) The A-H interval, which is measured from the onset of the A wave to the initial deflection of His bundle activation H in recording 36. This interval is a relatively accurate measure of conduction through the A-V node and typically is on the order of eighty-five milliseconds. (3) The H-V interval, which is taken from the onset of the His bundle deflection to the earliest appearing ventricular activity. The latter is indicated at V in His bundle electrogram 36 or at Q in surface electrocardiogram 34. This interval measures the conduction time through the specialized conduction system of the ventricular system (i.e., His bundle, bundle branches and major fascicles, and Purkinje fibers), and may typically be on the order of forty-five milliseconds.

During extensive experimentation which has been conducted in development of the instant invention, it has been found that proper selection of electrode placement locations for detecting His bundle signals is important, although not necessarily critical. More specifically, referring to FIG. 2, it has been found to be advantageous in many instances to locate the two electrodes connected to signal leads 18,20 (FIG. 1) either at locations A, being the third intercostal space to the left of the sternum and fifth intercostal space below the left nipple, or at locations A', being the fourth intercostal space to the left of the sternum and over the sixth rib on the right side. Th electrode connected to common lead 22 (FIG. 1) preferably is located at C over the sixth rib on the left side, with locations C' in the third and fifth intercostal spaces to the right of the sternum being advantageous alternatives in some instances. It is contemplated that the skilled medical technician will place the His bundle chest electrodes in other locations if conditions require, although as stated above the locations illustrated in FIG. 2 have been found acceptable in most instances. The manner of selecting locations for placement of the limb or chest electrodes for surface ECG recording is well known and is not illustrated in FIG. 2.

In accordance with an important feature of the invention, lowpass filter 24 and highpass filter 26 (FIG. 1) are separately adjustable at least in the range of 50 to 500 Hz, and preferably in the range of 30 to 600 Hz, to permit empirical adjustment by the technician or cardiologist in situ in accordance with conditions—e.g. patient muscle noise and extraneous electromagnetic interference. Most preferably, filter 24 posseses switch-selectable lowpass cut-off frequencies of 300–350 Hz, substantially 500 Hz and substantially 600 Hz. Filter 26 most preferably possesses switch-selectable highpass cut-off frequencies of substantially 30, 50 and 60 Hz. (All bandwidths and cut-off frequencies specified herein are the three-decibel-down bandwidths or frequencies as is conventional.) It is important to provide for separate highpass and lowpass frequency selection to accommodate empirical matching of the bandpass characteristics of the overall filter arrangement 28 in His channel 12 to each patient and the surrounding environment. The gain of amplifier 30 is also adjustable by the technician or cardiologist to provide a trace at 36 of workable amplitude.

FIG. 4 schematically illustrates presently preferred circuitry of switch-selectable lowpass and highpass filters 24,26. Highpass filter 26 includes a pair of operational amplifies IC1 and IC2 configured as a third order 18 db rolloff filter. A first three pole rotary switch S1 has first, second and third switch positions corresponding respective to filter settings of 31.8, 51 and 67 Hz as above-defined. First switch pole S1-A is connected at each switch position through a corresponding resistor R1–R3 to one input of amplifier IC1, the amplifier output being boot-strapped or fed back to the other input by the resistor R4. The output of amplifier IC1 is further connected to one input of amplifier IC2 through the series-connected filter capacitors C1,C2. The second and third poles S1-B and S1-C of switch S1 are connected at each of the three switch positions through the corresponding parallel-resistor networks R5–R7 and R8–R10 to the junction of capacitors C1,C2 and to the one input of amplifier IC2 respectively. The output of amplifier IC2 is fed back to the second amplifier input through a resistor R11, and thence to ground through a resistor R12.

Lowpass filter 24 includes a pair of operational amplifiers IC3 and IC4 also configured as a third order 18 db rolloff filter. A second three-pole rotary switch S2 has first, second and third switch positions corresponding respectively to filter settings of 284, 482 and 589 Hz as above-defined. One input of amplifier IC3 is connected through a first switch pole S2-A and at each switch position through a corresponding resistor R13–R15 to the output of IC2, and through a filter capacitor C3 to ground. The output of amplifier IC3 is boot-strapped to the other amplifier input by the resistor R16. The output of amplifier IC3 is connected to one input of amplifier IC4 through the parallel-resistor network R17–R19, through pole S2-B of switch S2, through the resistor network R20–R22 and then through switch pole S2-C. The common contact or wiper of switch pole S2-C is connected to ground through a filter capacitor C4, while the output of IC4 is boot-strapped to the common contact or wiper of switch pole S2-B by the filter capacitor C5. The output of amplifier IC4 is also fed back to the other amplifier input through resistor R23 in parallel with capacitor C6, and thence to ground through resistor R24. The input to filter 26 and the output of filter 24 are respectively connected to differential amplifier 16 and variable gain amplifier 30 (FIG. 1) as previously described.

From the foregoing description, it will be apparent that the preferred embodiment of the invention herein disclosed provides simultaneous continuous and non-invasive surface ECG and His bundle recording in real time, and fully satisfies all of the objects and aims previously set forth. The disclosed embodiment of the invention has been operated side-by-side with a conventional invasive-type His bundle recorder on a patient. The signals recorded in accordance with the invention were identical for all clinical purposes to those invasively obtained. It will be recognized, of course, that the recorded waveforms illustrated in FIG. 3 will vary from patient to patient, the particular waveforms and the manner of formulating a clinical diagnosis therefrom not constituting part of the present invention. Indeed, for various pathologies it may be expected that one or more of the various signal components illustrated in FIG. 3 will be distorted or absent altogether.

It will also be recognized that the invention is not limited to strip chart recorders per se, other means for real time recording and/or display being contemplated. For example, the surface and His bundle signals could be recorded on magnetic tape or the like for later playback analysis. Indeed, utilization of state-of-the-art solid state electronics (e.g. FIG. 4) renders the preferred embodiment of the invention readily adaptable for use in portable cassette-type ECG recorders and arrhythmia detectors. Alternatively, the analog signals at the outputs of amplifiers 10 and 30 could be fed to an analog-to-digital converter for recording in the memory of a digital computer for later retrieval and analysis.

An important aspect of the invention lies in the provision of separate switch-selectable high and lowpass filters; however, the invention is not limited to the specific circuitry illustrated in FIG. 4 or to the particular cutoff frequencies embodied therein. Rather, the circuitry of FIG. 4 illustrates a working embodiment which constitutes the best mode presently contemplated for practicing the invention. Other filter circuitry is contemplated having highpass and lowpass characteristics within the ranges previously set forth.

Nor is the invention limited in its broadest aspects to standard stress-test type chest electrodes, although such are preferred for reasons of economy and reliability. Unless otherwise limited, the term "electrode" in the appended claims must be read as encompassing all equivalent transducer means for providing the specified signals, the critical feature being that such signals are developed without invading the body of the patient. Indeed the invention is intended to embrace the above-noted and all other alternatives, modifications and variations as fall within the spirit and broad scope of the appended claims.

The invention claimed is:

1. A system for simultaneous real time recording of a patient's surface electrocardiogram and atrioventricular electrocardiogram comprising a plurality of surface electrodes adapted exclusively for non-invasive affixation at selected locations to the body of a patient, first means connected to said surface electrodes for developing electical signals as a function of the patient's surface electrocardiogram, second means including circuit means connected to said surface electrodes for developing exclusively from said surface electrodes electrical signals as a function of the patient's atrioventricular electrocardiogram, and recording means having at least first and second input channels respectively connected to said first and second means for simultaneously recording said surface and atrioventricular electrodcardiograms in real time on a common time base.

2. The system set forth in claim 1 wherein said circuit means includes adjustable bandpass filtering means for empirically tuning said circuit means to minimize extraneous electrical interference.

3. The system set forth in claim 2 wherein said bandpass filtering means is adjustable in a range of at least 50 to 50 Hertz.

4. Apparatus for recording the atrioventricular electrocardiogram of a patient comprising surface electrodes adapted for non-invasive affixation to a patient, signal display means and circuit means coupling said surface electrodes to said display means developing electrical signals representative of the patient's atrioventricular electrocardiogram exclusively from said surface electrodes and displaying said signals in real time, said circuit means including high gain amplifier means having bandpass filter means for passing signals to said display means at least in the range of 50 to 500 Hertz.

5. The invention set forth in claim 4 wherein said amplifier includes means for selectively adjusting amplifier gain.

6. The invention set forth in claim 2, 4 or 5 wherein said bandpass filtering means passes signals in the range 30 to 600 Hertz.

7. The invention set forth in claim 6 wherein said circuit means further comprises input means connected to receive signals from said electrodes and having an input impedance of over 100 megohms.

8. The invention set forth in claim 2 or wherein said bandpass filter means comprises separately variable high and lowpass filter means.

9. The invention set forth in claim 8 wherein said highpass filter means is variable in the range of 30 to 60 Hz and said lowpass filter means is variable in the range of 300 to 600 Hz.

10. The invention set forth in claim 9 wherein said highpass filter means comprises means incrementally variable to frequency settings of 30, 50 and 60 Hz, wherein said lowpass filter means comprises means incrementally variable to frequency settings of 300, 500 and 600 Hz, and wherein said circuit means further comprises switch means for selecting desired settings of said high and lowpass filter means independently of each other.

11. In a system for simultaneous recording of a patient's surface and atrioventricular electrocardiograms which includes strip chart recording means having at least two recording input channels and adapted to record in real time on a common time base waveforms indicative of electrical signals received at said input channels, and electrode means connected to said two recording input channels and adapted to be coupled to a patient for developing electrical signals as functions of the patient's surface and atrioventricular electrocardiograms, the improvement wherein said first recording channel includes means having a bandpass frequency range of at least 0.1 to 100 Hertz and said second recording channel includes means having a bandpass frequency range of at last 50 to 500 Hertz, and wherein said electrode means for developing said signals as a function of said atrioventricular electrocardiogram consist of surface-type electrode means adapted for non-invasive affixation at selected locations on the body of the patient.

12. The improvement set forth in claim 11 wherein said surface-type electrode means comprises stress test chest-type electrodes.

13. A non-invasive method of obtaining the atrioventricular electrocardiogram and surface electrocardiogram of a patient and recording said electrocardiograms simultaneously in real time comprising the steps of (a) placing surface electrodes at selected locations on a patient's body, (b) providing first and second analog amplifiers having respective inputs and outputs, each said analog amplifier being adapted to provide at its output an amplified replica of an analog signal fed to its corresponding input independently of the input to the other said amplifier, (c) connecting the input of said first amplifier to said surface electrodes to develop at the output of said first amplifier a continuous amplified analog replica of the patient's surface electrocardiogram solely as a function of signals fed to said first amplifier from said surface electrodes, (d) connecting the input of said second amplifier to said surface electodes to develop at the output of said second amplifier a continuous amplified analog replica of the patient's atrioventricular electrocardiogram solely as a function of signals fed to said second amplifier input from said surface electrodes, and (e) directing said continuous amplified analog outputs of said first and second amplifiers to corresponding channels of a multiple-channel strip chart recorder for recording both said electrocardiograms in real time in parallel channels on said recorder on a common time base.

14. The method set forth in claim 13 wherein said second amplifier means includes adjustable bandpass filtering means with a maximum bandpass range of 30 to 600 Hz, and wherein said method includes the additional step of empirically adjusting said filtering means to record a said atrioventricular electrocardiogram of optimum clarity.

15. A non-invasive method of recording in real time the atrioventricular electrocardiogram of a human patient comprising the steps of:
 (a) affixing surface electrodes at selected locations on a patient's body,
 (b) providing an analog amplifier having an input, an output and a bandpass frequency range of at least 50 to 500 Hertz,
 (c) connecting the input of said amplifier to said surface electrodes to develop at said output in real time a continuous analog replica of the patient's atrioventricular electrocardiogram exclusively as a function of the input to said amplifier from said surface electrodes, and
 (d) connecting said amplifier output to real time recording means to record said continuous analog replica of said atrioventricular electocardiogram.

16. The method set forth in claim 15 wherein said amplifier has separately adjustable highpass and lowpass cut-off frequencies, and wherein said method comprises the additional step of empirically adjusting said amplifier highpass and lowpass cut-off frequencies while observing said continuous analog replica recorded in said step (c) to optimize said recorded replica.

* * * * *